United States Patent
Hendricks

(12) 
(10) Patent No.: US 6,790,462 B2
(45) Date of Patent: Sep. 14, 2004

(54) CALCIUM DIETARY SUPPLEMENT

(75) Inventor: Lewis Hendricks, Richboro, PA (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 10/214,635

(22) Filed: Aug. 8, 2002

(65) Prior Publication Data

US 2003/0031726 A1 Feb. 13, 2003

Related U.S. Application Data

(60) Provisional application No. 60/311,008, filed on Aug. 9, 2001.

(51) Int. Cl.$^7$ .................. A61K 33/06; A61K 33/10; A61K 33/02; A61K 9/14; A61K 9/20
(52) U.S. Cl. .................. 424/602; 424/464; 424/489; 424/687; 514/167; 514/168; 514/249; 514/345; 514/52; 514/819; 514/825; 514/904; 514/905; 514/960
(58) Field of Search .................. 424/464, 489, 424/602–606, 687, 682, 686; 574/167, 168, 249, 345, 52, 819, 825, 904, 905, 960

(56) References Cited

U.S. PATENT DOCUMENTS

| | | | |
|---|---|---|---|
| 4,751,085 A | 6/1988 | Gaull | 424/145 |
| 4,781,925 A | 11/1988 | Michelucci et al. | 424/465 |
| 5,340,603 A | 8/1994 | Neylan et al. | 426/73 |
| 5,480,872 A | 1/1996 | Cope et al. | 514/21 |

FOREIGN PATENT DOCUMENTS

WO          00/28973      *  5/2000

OTHER PUBLICATIONS

Chemical Abstracts 139:213468 (2003).*
Chemical Abstracts 134:366115 (2001).*
Medline Abstract, Accession No. 94003720 (1994).*
Database Google, Product Information Sheet on TVM Plus (Multivitamin), www.cybervitamins.com.com, 1995.
Database Google, Product Information Sheet on Posture–D, www.drugstore.com, 1999.
Database HCAPLUS on STN, No. 1982:51078, Guenther et al. 'Effect of Vitamin D3 on the Useability of Mineral Phosphorus Compounds,' abstract, Kraftfutter, 1981, 64(10), 500,m 506–6, 508.
Database HCAPLUS on STN, No. 1981:423212, Lee et al. 'Effects of Supplementation of the Diets with Calcium and Calcium–Rhich Foods on Bone Density of Elderly Females with Osteoporosis,' abstract, American Journal of Clinical Nutrition, 1981, 34(5), 819–23.
Database HCAPLUS on STN, No. 1964:63083, Chandler et al. 'Investigation of Calcium , Phosphorus, and Vitamin D3 Relations in Rats by Multiple Regression Techniques,' abstract, J. Nutr. 1962, 78, 28–36.

* cited by examiner

*Primary Examiner*—John Pak

(57) ABSTRACT

A dietary supplement composition contains phosphorus and from greater than 1.3 to less than 2.2 parts by weight calcium per part by weight phosphorus, and may, optionally, further contain Vitamin D, Vitamin $B_{12}$, folate and Vitamin $B_6$, provides components that have been linked to bone health.

20 Claims, No Drawings

CALCIUM DIETARY SUPPLEMENT

This application claims benefit of Provisional 60/311,008 filed Aug. 9, 2001.

FIELD OF THE INVENTION

This invention relates to dietary supplements, more particularly to calcium-containing dietary supplements.

BACKGROUND OF THE INVENTION

Mineral and vitamin compositions are routinely used as dietary supplements, either as general nutritional supplements or as therapeutic preparations directed to treat specific medical problems.

Calcium is an important nutrient for growing children to help in bone formation and for adults to help prevent bone loss. Excessive bone loss may lead to a condition known as "osteoporosis", in which decreased bone mass causes the bones to be more brittle and thus more susceptible to fracture. It is widely believed that a chronic shortage of dietary calcium is one factor leading to osteoporosis, see *Osteoporosis, Cause, Treatment, Prevention*, U.S. Dept. of Health and Human Services, Public Health Service National Institutes of Health, Maryland 1987. Calcium dietary supplements appear to be of value in helping to prevent osteoporosis.

It also has been suggested that, in addition to calcium, other minerals, such as copper, magnesium and zinc, and certain vitamins, such as vitamin D, play important roles in bone formation and metabolism, see, for example, Strause, L., et. al., "The Role of Trace Elements in Bone Metabolism", *Nutritional Aspects of Osteoporosis*, New York, Raven Press, p. 223–233, 1992.

Furthermore, there is evidence that elevated levels of homocysteine (Hcy), an amino acid that is formed as a byproduct of metabolism and is found in the blood plasma, provide a better indicator for coronary heart disease than elevated blood cholesterol levels (see McCully, K, *The Homocysteine Revolution, New Canaan, Conn.: Keats Publishing*, 1997). It has also been found that the B-complex vitamins administered as nutritional supplements can be effective in reducing plasma levels of Hcy.

A possible link between elevated Hcy and the progression of osteoporosis can be inferred from the effects of two osteoporosis treatments, hormone replacement therapy (HRT) and raloxifene hydrochloride. HRT is an effective treatment for the prevention of osteoporosis, but has an additional documented effect of reduction of Hcy levels as well (see Mijatovic V, van der Mooren M J, "Homocysteine in postmenopausal women and the importance of hormone replacement therapy", *Clin Chem Lab Med* 2001 August;39 (8): 764–7). Raloxifene hydrochloride belongs to a class of drugs described as selective estrogen receptor modulators, and in addition to its well documented benefits in the treatment of osteoporosis, it has been shown in two randomized trials on post-menopausal women to reduce Hcy levels (see Saitta A et al, "Cardiovascular effects of raloxifene hydrochloride", *Cardiovasc Drug Rev* 2001 Spring;19 (1):57–74).

It has been postulated that elevated levels of Hcy are implicated in many of the diseases associated with aging such as the decline in cognitive abilities, occlusive vascular disease and events leading to osteoporosis by virtue of the formation of adducts with metabolically important molecules, primarily proteins (see Krumdieck C L, Prince C W, "Mechanisms of homocysteine toxicity on connective tissues: implications for the morbidity of aging", *J Nutr* 2000 February;130(2S Suppl.):365S–368S). This irreversible homocysteinylation leads to a reduction or complete loss of function of these proteins which is time and Hcy concentration dependent. Thus the reduction of Hcy achieved through use of suitably formulated nutritional supplements may retard or prevent the progression of these molecular changes to the point where they are manifested as clinical impairment.

There a continuing interest in providing improved calcium dietary supplements which contain other components in addition to calcium in order to promote healthy bone growth and slow or prevent bone loss.

SUMMARY OF THE INVENTION

In a first aspect, the present invention is directed to a dietary supplement composition, comprising phosphorus and from greater than 1.3 to less than 2.2 parts by weight calcium per part by weight phosphorus.

In a second aspect, the present invention is directed to a particulate dietary supplement composition, comprising phosphorus and from greater than 1.3 to less than 2.2 parts by weight calcium per part by weight phosphorus.

In a third aspect, the present invention is directed to a directly compressible dietary supplement composition, comprising phosphorus, from greater than 1.3 to less than 2.2 parts by weight calcium per part by weight phosphorus, a dissolution aid and a lubricant, wherein said directly compressible dietary supplement composition is capable of being directly compressed to form tablet of dietary supplement composition.

In a fourth aspect, the present invention is directed to a dietary supplement composition in tablet form, comprising calcium and phosphorus, wherein the tablet has a total weight of from 400 to 2000 milligrams per tablet and comprises greater than about 200 milligrams calcium per tablet and from greater than 1.3 to less than 2.2 parts by weight calcium per part by weight phosphorus.

In a fifth aspect, the present invention is directed to a liquid dietary supplement composition, comprising calcium and phosphorus, wherein the liquid comprises greater than about 100 milligrams calcium per 100 milliliters of liquid and from greater than 1.3 to less than 2.2 parts by weight calcium per part by weight phosphorus.

In a sixth aspect, the present invention is directed a dietary supplement composition comprising phosphorus, from greater than 1.3 to less than 2.2 parts by weight calcium per part by weight phosphorus and a compound selected from Vitamin D, Vitamin $B_{12}$, folate and Vitamin $B_6$.

Comparison of daily calcium intake and daily phosphorus intake set forth in IOM Daily Reference Intakes of Ca, P, Mg and F, 1997, pp. 390–391 (ISBN 0-309-06403-1) with the recommended daily intakes set forth in 21 U.S. Code of Federal Regulations 101.9 reveals a correlation between calcium and phosphorus deficiencies, particularly among women from 31 to 70 years of age and among children from 4 to 8 years of age. The supplement composition of the present invention provides supplemental calcium and phosphorus in the relative amounts required to simultaneously correct the calcium and phosphorus deficiencies which characterize the demographic group of those women greater than 31 years of age that are in the $50^{th}$ percentile or lower in calcium and phosphorus intake. In preferred embodiments, the supplement composition of the present invention combines the benefits of supplemental calcium and phosphorus in the above described ratios with the effects of certain B-complex vitamins to provide further benefit in the prevention of osteoporosis in men and women.

DETAILED DESCRIPTION OF INVENTION AND PREFERRED EMBODIMENTS

In a preferred embodiment, the dietary supplement composition of the present invention comprises greater than about 20 parts by weight ("pbw"), more preferably from about 25 to about 35 pbw, and even more preferably from 28 to about 32 pbw calcium per 100 pbw of the supplement composition.

In a preferred embodiment, the supplement composition of the present invention comprises from about 1.4 to about 2.1 pbw, more preferably from about 1.5 to about 2.0 pbw, calcium per pbw phosphorus.

In a preferred embodiment, the calcium component of the supplement composition of the present invention comprises one or more of calcium chelates, such as for example, calcium proteinate, and calcium salts, such as, for example, calcium carbonate, calcium gluconate, calcium citrate, tricalcium phosphate, or dicalcium phosphate dihydrate or anhydrous dicalcium phosphate, calcium citrate maleate.

In a preferred embodiment, the phosphorus component of the supplement composition of the present invention comprises one or more of phosphate salts, such as for example, tricalcium phosphate, or dicalcium phosphate dihydrate or anhydrous dicalcium phosphate, sodium phosphate, and proteins, such as, for example, soy protein, whey protein.

In a preferred embodiment, the phosphorus component and a portion of the calcium component of the supplement composition of the present invention are supplied as a calcium phosphate salt, such as for example, tricalcium phosphate, dicalcium phosphate dihydrate, anhydrous dicalcium phosphate, monocalcium phosphate.

In a preferred embodiment, the calcium and phosphorus components are each in the form of particles, more preferably particles having an average particle size of from about 180 to about 350 micrometers ($\mu$m).

In a preferred embodiment, the dietary supplement composition of the present invention comprises anhydrous dicalcium phosphate, tricalcium phosphate and calcium carbonate.

In a highly preferred embodiment, the dietary supplement composition of the present invention comprises, based on 100 pbw of the composition, from about 50 to about 70 pbw, more preferably from about 56 to about 65 pbw, and even more preferably from about 59 to about 62 pbw, anhydrous dicalcium phosphate, from about 24 to about 40 pbw, more preferably from about 28 to about 36 pbw, and even more preferably from about 31 to about 33 pbw, tricalcium phosphate and from about 3 to about 11 pbw, more preferably from about 5 to about 9 pbw, and even more preferably from about 6 to about 8 pbw, calcium carbonate.

In a preferred embodiment, the dietary supplement composition is capable of being directly compressed to form a compressed oral dosage from, such as, for example, a tablet or caplet, and comprises, based on 100 pbw of the composition, from about 50 to about 70 pbw, more preferably from about 56 to about 65 pbw, and even more preferably from about 59 to about 62 pbw, anhydrous dicalcium phosphate, from about 24 to about 40 pbw, more preferably from about 28 to about 36 pbw, and even more preferably from about 31 to about 33 pbw, tricalcium phosphate and from about 3 to about 11 pbw, more preferably from about 5 to about 9 pbw, and even more preferably from about 6 to about 8 pbw, calcium carbonate, from about 1 to about 3 pbw dissolution aid, and from about 0.5 to about 2 pbw lubricant.

In a preferred embodiment, the supplement composition further comprises dietary supplemental amounts of vitamins or minerals other than calcium or phosphorus. In a highly preferred embodiment, the supplement composition comprises a dietary supplemental amount of one or more vitamins, such as for example, vitamin D, Vitamin $B_6$; folate and Vitamin $B_{12}$, phytoestrogens, such as for example, one or more isoflavones, one or more probiotics and prebiotics, such as for example lactobacillus acidophilus, inulin or other polysaccharides and one or more minerals other than calcium or phosphorus, such as for example, boron, copper, zinc, magnesium, manganese and zinc, that play a role in bone formation and/or bone metabolism. Alternatively, the supplement composition of the present composition may be included as a component of a multi-vitamin and mineral supplement composition.

In one embodiment, the dietary supplement composition comprises calcium and phosphorus and further comprises one or more of Vitamin D, Vitamin $B_6$, folate and Vitamin $B_{12}$.

In a preferred embodiment, the composition comprises, based on 100 pbw of the composition, from about 6.2 to about 62 pbw, more preferably from about 15.5 to about 47 pbw, and even more preferably from about 29 to about 33 pbw, calcium and from about 6.2 to about 55.7 pbw, more preferably from about 9.3 to about 55.7 pbw and even more preferably from about 16 to about 20 pbw, phosphorus.

In a preferred embodiment, the composition comprises, based on 100 pbw of the composition, from about 0.000039 to about 0.0012 pbw, more preferably from about 0.00019 to about 0.00062 pbw, and even more preferably from about 0.00025 to about 0.00035 pbw, Vitamin D (as cholecalciferol).

In a preferred embodiment, the composition comprises, based on 100 pbw of the composition, from about 0.03 to about 6.2 pbw, more preferably from about 0.15 to about 4.64 pbw, and even more preferably from about 0.30 to about 0.60 pbw, Vitamin $B_6$.

In a preferred embodiment, the composition comprises, based on 100 pbw of the composition, from about 0.0016 to about 0.062 pbw, more preferably from about 0.0062 to about 0.046 pbw and even more preferably from about 0.025 to about 0.035 pbw, folate (as folic acid);

In a preferred embodiment, the composition comprises from about 0.000031 to about 0.037 pbw, more preferably from about 0.00019 to about 0.031 pbw and even more preferably from about 0.01 to about 0.03 pbw, Vitamin $B_{12}$ (as cyanocobalamin).

The supplement composition of the present invention may, optionally, contain other ingredients generally recognized as safe for food additive use, including for example, preservatives, such as, for example, butylated hydroxytoluene, butylated hydroxyanisole, food grade emulsifiers, such as, for example, lecithin, propylene glycol esters, and pharmaceutically acceptable carriers and excipients, such as for example, binders, fillers, lubricants, dissolution aids.

The supplement composition of the present invention is made by combining calcium and phosphorus components, as well as any optional components, in the desired relative amounts and mixing the components according to known methods to produce a substantially homogeneous mixture.

The present supplement composition may be administered in any oral dosage form, including liquid dosage forms such as, for example, a suspension or slurry, and oral solid dosage forms such as, for example, a tablet or bulk powder. As used herein the term "tablet" refers generally to tablets, caplets, capsules, including soft gelatin capsules, and lozengers.

In a preferred embodiment, the supplement composition of the present invention is administered in the form of a tablet. More preferably, the supplemental composition is administered in the form of a tablet of less than or equal to 2 grams per tablet, more preferably from 400 to 1900 mg per tablet, which contains greater than about 225 mg, more preferably from about 250 mg to about 800 mg, calcium per tablet.

Tablets are made by methods known in the art and may further comprise suitable binders, lubricants, diluents, disintegrating agents, colorants, flavoring agents, flow-inducing agents, melting agents which are known in the art. The oral solid dosage form may, optionally, have a film coating to protect the components of the supplement Composition from one or more of moisture, oxygen and light or to mask any undesirable taste or appearance. Suitable coating agents include, for example, cellulose, hydroxypropylmethyl cellulose.

EXAMPLE 1

The supplement composition of Example 1 was made by mixing 1174.8 grams (g) anhydrous dicalcium phosphate, 629.9 g tricalcium phosphate, 134.7 g calcium carbonate, 40.1 g dissolution aid (AC DI-SOL™ crosscarmellose sodium) and 20.1 g lubricant (magnesium stearate) in a V-blender. The mixture exhibited a bulk density of 0.859 grams per cubic centimeter and a tamped density of 0.943 grams per cubic centimeter.

The mixture was compressed to form tablets of about 950 mg or about 1900 mg each. The 950 mg tablets each contained about 300 mg calcium and 175 mg phosphorus per tablet. The 1900 mg tablets each contained about 600 mg calcium and 350 mg phosphorus per tablet.

The dissolution properties of the tablets were determined by <711> Dissolution, USP 24, p 1941 (2000) in 0.1N HCl at 37° C. for a test period of 45 minutes. Results are set forth below in TABLE I as tablet weight, expressed in milligrams (mg), results of analysis of the dissolution medium by Inductively Coupled Plasma Spectrophotometer ("ICP Results"), expressed in milligrams of calcium or phosphorus per gram of tablet powder (mg/g), and in milligrams (mg) per 900 milliliters of dissolution medium and the "Label Claim" amount, calculated from the total amount of calcium or phosphorus (in mg) in 900 ml of dissolution medium and expressed as a percentage of the initial tablet weight.

TABLE I

| Tablet # | Tablet Weight (mg) | ICP Results (mg/gm) Ca | P | In 900 ml (mg) Ca | P | Label Claim (%) Ca | P |
|---|---|---|---|---|---|---|---|
| 1 | 946.3 | 321 | 195 | 288.9 | 175.5 | 96.3 | 100.3 |
| 2 | 944.8 | 311 | 188 | 279.9 | 169.2 | 93.3 | 96.7 |
| 3 | 940.2 | 310 | 188 | 279.0 | 169.2 | 93.0 | 96.7 |
| 4 | 941.7 | 315 | 188 | 283.5 | 169.2 | 94.5 | 96.7 |
| 5 | 951.4 | 322 | 189 | 289.8 | 170.1 | 96.6 | 97.2 |
| 6 | 940.8 | 320 | 191 | 288.0 | 171.9 | 96.0 | 98.2 |

TABLE I-continued

| Tablet # | Tablet Weight (mg) | ICP Results (mg/gm) Ca | P | In 900 ml (mg) Ca | P | Label Claim (%) Ca | P |
|---|---|---|---|---|---|---|---|
| 7 | 1890.8 | 583 | 354 | 524.7 | 318.6 | 87.5 | 91.0 |
| 8 | 1894.5 | 570 | 338 | 513.0 | 304.2 | 85.5 | 86.9 |
| 9 | 1901.0 | 582 | 350 | 523.8 | 315.0 | 87.3 | 90.0 |
| 10 | 1897.9 | 572 | 344 | 514.8 | 309.6 | 85.8 | 88.5 |
| 11 | 1895.0 | 534 | 313 | 480.6 | 281.7 | 80.1 | 80.5 |

EXAMPLE 2

The supplement composition of Example 2 was made by mixing 1148.2 grams (g) anhydrous dicalcium phosphate, 613.7 g tricalcium phosphate, 131.2.7 g calcium carbonate, 0.4 g Vitamin D 100 CWS (Roche®#65242) encapsulated powder, 9.3 g Vitamin $B_6$, 6.2 g of 10% triturated folic acid, 30.9 g of 1% triturated Vitamin $B_{12}$, 40.1 g dissolution aid (AC DI-SOL™ crosscarmellose sodium) and 20.0 g lubricant (magnesium stearate) in a V-blender.

The mixture was compressed to form tablets of about 808 mg each. The 808 mg tablets contained about 1000 mg calcium, 583 mg phosphorus, 400 IU Vitamin D, 15 mg Vitamin $B_6$, 1000 mcg folic acid and 500 mcg Vitamin $B_{12}$ per 4 tablets. This mixture ran well on a Manesty B3B rotary tablet press in $\frac{7}{16}$" round dies, and exhibited an average tablet hardness of 14.7 kP when compressed with 28.9 kN force.

The supplement composition of the present invention provides supplemental calcium and phosphorus in the relative amounts required to simultaneously correct the calcium and phosphorus deficiencies which characterize the demographic group of those women greater than 31 years of age that are in the $50^{th}$ percentile or lower in calcium and phosphorus intake.

What is claimed is:

1. A dietary supplement composition, comprising phosphorus and from greater than 1.3 to less than 2.2 parts by weight calcium per part by weight phosphorus, wherein the composition comprises, based on 100 parts by weight of the composition, from about 50 to about 70 parts by weight anhydrous dicalcium phosphate, from about 24 to about 40 parts by weight tricalcium phosphate, and from about 3 to about 11 parts by weight calcium carbonate.

2. The composition of claim 1, wherein the composition comprises greater than about 20 parts by weight calcium per 100 parts by weight of the supplement composition.

3. The composition of claim 1, wherein the composition comprises from about 25 to about 35 parts by weight calcium per 100 parts by weight of the supplement composition.

4. The composition of claim 1, wherein the composition comprises from 28 to about 32 parts by weight calcium per 100 parts by weight of the supplement composition.

5. The composition of claim 1, wherein the composition comprises from about 1.4 to about 2.1 parts by weight calcium per part by weight phosphorus.

6. The composition of claim 1, wherein the composition comprises from about 1.5 to about 2.0 per part by weight calcium per part by weight phosphorus.

7. The composition of claim 1, wherein the composition comprises, based on 100 parts by weight of the composition, from about 56 to about 65 parts by weight anhydrous dicalcium phosphate, from about 28 to about 36 parts by weight tricalcium phosphate, and from about 5 to about 9 parts by weight calcium carbonate.

8. The composition of claim 1, further comprising one or more compound selected from the group consisting of vitamin D, Vitamin $B_6$; folate, and Vitamin $B_{12}$.

9. The composition of claim 1, wherein the composition is in particulate form.

10. The composition of claim 1, wherein the composition is in liquid form.

11. The composition of claim 10, wherein the composition is in the form of a liquid comprising greater than about 100 milligrams calcium per 100 milliliters of the liquid.

12. The composition of claim 1, wherein the composition is in tablet form.

13. The composition of claim 12, wherein the composition is in the form of one or more tablets having a total weight of from 400 to 2000 milligrams per tablet and comprising greater than about 200 milligrams calcium per tablet.

14. The composition of claim 13 wherein the one or more tablets have a total weight of from 400 to 1900 mg per tablet and comprise greater than about 225 mg calcium per tablet.

15. The composition of claim 13, wherein the one or more tablets have a total weight of from 400 to 1900 mg per tablet and comprise from about 250 mg to about 800 mg calcium per tablet.

16. The composition of claim 13, further comprising one or more compound selected from the group consisting of Vitamin D, Vitamin $B_6$; folate, and Vitamin $B_{12}$.

17. A directly compressible dietary supplement composition, comprising phosphorus, from greater than 1.3 to less than 2.2 parts by weight calcium per part by weight phosphorus, wherein the composition comprises, based on 100 parts by weight of the composition, from about 50 to about 70 parts by weight, anhydrous dicalcium phosphate, from about 24 to about 40 parts by weight tricalcium phosphate from about 3 to about 11 parts by weight calcium carbonate, from about 1 to about 3 parts by weight of a dissolution aid, and from about 0.5 to about 2 parts by weight a lubricant and wherein said directly compressible dietary supplement composition is capable of being directly compressed to form tablet of dietary supplement composition.

18. The composition of claim 17, wherein the composition comprises, based on 100 parts by weight of the composition, from about 56 to about 65 parts by weight anhydrous dicalcium phosphate, from about 28 to about 36 parts by weight tricalcium phosphate, from about 5 to about 9 parts by weight calcium carbonate, from about 1 to about 3 parts by weight dissolution aid, and from about 0.5 to about 2 parts by weight lubricant.

19. The composition of claim 17, wherein the composition comprises, based on 100 parts by weight of the composition, from about 59 to about 62 parts by weight anhydrous dicalcium phosphate, from about 31 to about 33 parts by weight tricalcium phosphate, from about 6 to about 8 parts by weight calcium carbonate, from about 1 to about 3 parts by weight dissolution aid, and from about 0.5 to about 2 parts by weight lubricant.

20. The composition of claim 17, further comprising one or more compound selected from the group consisting of Vitamin D, Vitamin $B_6$; folate and Vitamin $B_{12}$.

* * * * *